United States Patent [19]

McNulty et al.

[11] 4,104,273

[45] Aug. 1, 1978

[54] DERIVATIVES OF 3-CYANO-PYRID-2-ONES

[75] Inventors: Patrick J. McNulty, Wyndmoor; Harlow L. Warner, Hatboro, both of Pa.

[73] Assignee: Rohm and Haas Company, Philadelphia, Pa.

[21] Appl. No.: 777,989

[22] Filed: Mar. 16, 1977

Related U.S. Application Data

[62] Division of Ser. No. 513,988, Oct. 11, 1974, Pat. No. 4,028,084.

[51] Int. Cl.$^2$ ............... C07D 213/57; A01N 9/22
[52] U.S. Cl. ................. 260/294.9; 260/295.5 R; 71/94
[58] Field of Search ....................... 260/294.9

[56] References Cited

U.S. PATENT DOCUMENTS

| | | | |
|---|---|---|---|
| 2,947,754 | 8/1960 | Scudi et al. | 260/295.5 R |
| 3,576,814 | 4/1971 | Seidel et al. | 260/295.5 R |

OTHER PUBLICATIONS

Seidel et al., Chem. Abstracts, vol. 72, (No. 5), 21616g, Feb. 2, 1970.

*Primary Examiner*—Alan L. Rotman
*Attorney, Agent, or Firm*—Bernard J. Burns; William E. Lambert; George W. F. Simmons

[57] ABSTRACT

Novel compounds belonging to the class of 1-substituted benzylpyrid-2-one-4,6-dialkyl and 4,5,6-trisubstituted-3-carboxylic acids, amides, esters and physiologically acceptable salts. These compounds possess biological activity and in particular are gametocides and plant growth regulators.

Novel 1-substituted benzyl-3-cyano-4,5,6-trisubstituted pyrid-2-ones are also disclosed as intermediates.

1 Claim, No Drawings

DERIVATIVES OF 3-CYANO-PYRID-2-ONES

This is a division of application Ser. No. 513,988, filed Oct. 11, 1974, now U.S. Pat. No. 4,028,084 granted June 7, 1977.

SUMMARY OF THE INVENTION

This invention is concerned with novel organic compounds belonging to the general class of 1-benzylpyrid-2-ones. It also relates to the biological activity of these structures. In particular they are useful as plant growth regulators and gametocidal agents.

The cereal grains, such as corn, wheat, rice and barley are among the major food crops throughout the world. This importance has led to extensive research to improve both the productivity and food value of these crops. One of the most important approaches taken to improve the quality of the cereal grains has been hybridization. While hybridization has been an effective technique for some crops, most notably corn, there have been a number of problems with present techniques. For example, corn hybridization requires time-consuming hand detasseling or inefficient mechanical detasseling, possibly injuring the corn plant. Corn, barley, and wheat hybridization by means of cytoplasmic male sterile varieties can only be done with a limited genetic base, requiring a maintainer line and a restorer line. Furthermore, cytoplasmic male sterile techniques with barley and wheat necessitate a highly sophisticated approach to deal with the genetic complexities of these crops, and great success has not yet been achieved in developing a suitable approach. Since the induction of selective male sterility by chemical means would obviate many of the problems confronting the present hybridization techniques, new compounds which produce the desired sterility would be extremely desirable in dependably and economically supplying the male sterile plants needed for hybridization.

A new class of compounds has now been found which can be used to induce male sterility in cereal grains. The compounds of the invention are 1-benzylpyrid-2-ones which may be depicted by the formula:

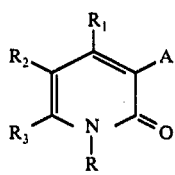

wherein A is a cyano group or

wherein Y is a halogen atom, an amino group, a hydroxy group or an alkoxy group; $R_1$, $R_2$ and $R_3$ are a hydrogen atom a methyl or ethyl group; R is a group of the formula

wherein X is a hydrogen atom, an amino group, a halogen atom, a trifluoromethyl group, a nitro group or an alkyl group; n is 0–2.

The term alkoxy in the above definition of Y is an alkyl group of from 1 to 7 carbon atoms which can be straight chained or branched. The term "alkyl" in the definition of X is an alkyl group of from 1 to 4 carbon atoms which can also be straight chained or branched.

Any suitable physiologically acceptable basic addition salts of the carboxylic acids of this invention can be utilized. Typical salt can be sodium, potassium, ammonium, dimethylammonium, diethylammonium, etc.

The preferred compounds of this invention are where $R_2$ is hydrogen. The more preferred compounds of this invention are where A is carboxyl while $R_2$ is hydrogen and the physiologically acceptable salts thereof. The most preferred compounds of this invention are where $R_1$ and $R_2$ are methyl while A is carboxyl and $R_2$ is hydrogen and the physiologically acceptable salts thereof.

Typical compounds within the scope of this invention include:

1-benzyl-3-carboxy-6-methylpyrid-2-one
1-(2-chlorobenzyl)-3-carboxy-4,6-dimethylpyrid-2-one
1-(3-bromobenzyl)-3-carboxy-6-methylpyrid-2-one
1-(4-nitrobenzyl)-3-carboxy-4,6-dimethylpyrid-2-one
1-(2,4-dichlorobenzyl)-3-carboxy-4,6-dimethylpyrid-2-one
1-(3,4-dichlorobenzyl)-3-carboxy-4,6-dimethylpyrid-2-one
1-(2,5-dibromobenzyl)-3-carboxy-6-ethylpyrid-2-one
1-(4-trifluoromethylbenzyl)-3-carboxy-4,6-diethylpyrid-2-one and physiologically acceptable salts thereof
1-(2-methylbenzyl)-3-cyano-4,6-dimethylpyrid-2-one
1-(3-ethylbenzyl)-3-cyano-6-methylpyrid-2-one
1-(4-isopropylbenzyl)-3-carbamoyl-6-ethylpyrid-2-one
1-(2,4-dimethylbenzyl)-3-carbamoyl-4,6-dimethylpyrid-2-one
1-(2,5-diethylbenzyl)-3-carbomethoxy-4,6-dimethylpyrid-2-one
1-(3,4-dimethylbenzyl)-3-carboethoxy-4,6-dimethylpyrid-2-one
1-(2-aminobenzyl)-3-carbomethoxy-6-methylpyrid-2-one The compounds of this invention may be prepared by the following reaction scheme:

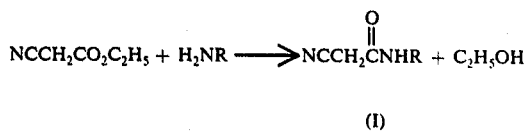

(I)

-continued

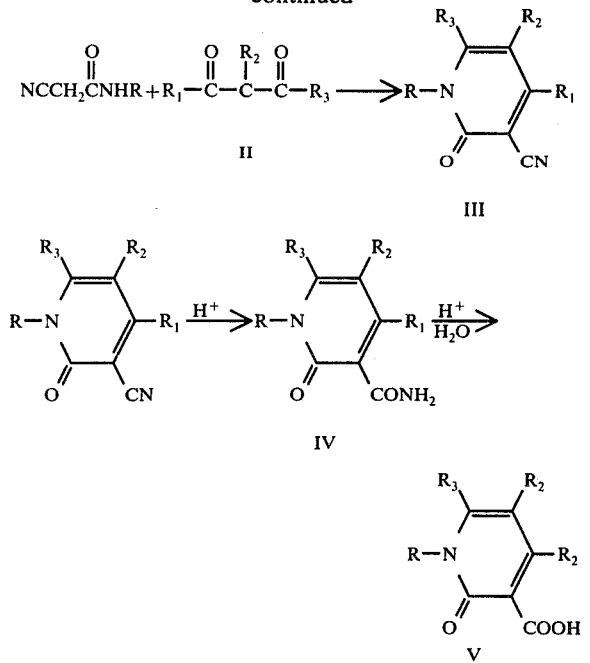

N-benzylcyanoacetamides (Formula I) are known compounds which may be made by heating ethyl cyanoacetate with the appropriate benzylamine usually under neat conditions, and removing the ethanol as formed according to the above reaction scheme. This is usually a facile reaction in the temperature range of 150°–250° C. The end of the reaction is judged when the removal of ethanol is essentially completed. The reaction product may be used without further purification. Refer to Piccinini et al., Chemishes Zentralblatt 78,335 (1907).

The beta-diketones (Formula II) may be made by the general methods described by J. T. Adams et al., J. Chem. Soc. 66,1220 (1944) and A. W. Johnson et al., Organic Synthesis 42,75 (1962). Pentane-2,4-dione is a product of commerce.

The 1-benzyl-3-cyanopyrid-2-ones (Formula III) may be prepared by condensation of beta diketones (Formula II) with N-benzyl cyanoacetamides (Formula I) in the presence of a basic catalyst.

In the condensation of beta-diketone with the N-benzyl acetamide equimolar amounts of the two reactants are normally used, although excesses of either reagent are permissible. In some instances, it may be expedient to use an excess of the beta-diketone.

The condensation of the beta-diketone with an N-benzyl cyanoacetamide is preferably carried out in the presence of a solvent. Suitable solvents include alcohols, ethers, aliphatic hydrocarabons, dimethylformamide, dimethyl sulfoxide and carbon tetrachloride. The preferred solvents are the alcohols such as methanol, ethanol, isopropanol and monoethers of ethylene glycol. Heat is required for the condensation and this is usually obtained at the reflux temperature of the solvent used. Temperatures in the range of 50° to 150° C. are suitable.

The condensation of the beta-diketone with an N-benzyl cyanoacetamide is catalyzed by basic catalysts. Typical catalysts include inorganic bases, amines and quaternary ammonium hydroxides. Amine catalysts are preferred and good results have been obtained with piperidine, pyridine, diethylamine and triethylamine for example. General conditions for this type of condensation are reviewed in "Heterocyclic Compounds," edited by A. Weissberger, Interscience Publishers, 1962, in Part III on "Pyridinols and Pyridones," pages 525–531.

The 1-benzyl-3-cyano-pyrid-2-ones can also be prepared by the general method described in the above cited book "Heterocyclic Compounds" on page 596. This consists of quaternizing a 3-cyanopyridine with an iodoalkane in a solvent having a high dielectric constant, such as acetonitrile, and oxidizing the resulting pyridinium salt with alkaline potassium ferricyanide to the corresponding α-pyridone. The reaction may be depicted as follows:

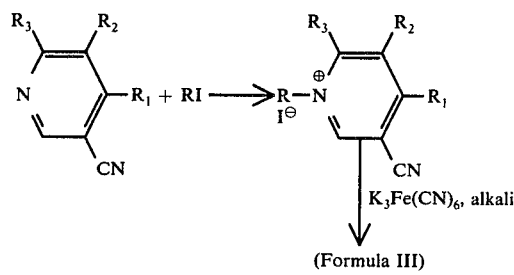

(Formula III)

The 1-benzyl-3-cyano-4,6-dimethylpyrid-2-ones may also be prepared by a ring-closure procedure generally described in the above cited book "Heterocyclic Compounds" on page 551. The reaction may be depicted for the 3-methoxycarbonyl compounds as follows:

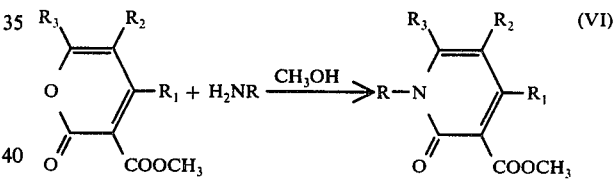

The compounds of (Formula VI) may be converted to the corresponding carboxy compounds or their water-soluble salts by standard hydrolytic procedures.

The hydrolysis of 1-benzyl-3-cyano-pyrid-2-ones may proceed to either the amide (Formula IV) or the acid (Formula V) under acidic conditions. Aqueous organic and mineral acids are suitable for this purpose. Typical of such acids are formic, acetic, hydrochloric, hydrobromic, sulfuric and phosphoric. The temperature must be high enough to allow the hydrolysis to proceed but not sufficiently high to cause decarooxylation. This is normally in the range of 50° to 150° C., with a preferred range of 80° to 120° C. The cyano compounds of (Formula III) can be converted to the carbamoyl derivatives of (Formula IV) by hydrolysis with hydrogen peroxide in dilute base or by other methods known in the art. The carbamoyl derivatives can be hydrolyzed to the free acids of (Formula V) by means of nitrous acid or by other hydrolytic procedures well known in the chemical art.

The acids of Formula V are readily converted to derivatives. For example, direct esterification with alcohols gives esters and reaction with halogenating agents such as oxalylchloride, thionyl chloride or bromide and phosphorus pentachloride gives the acid halides. The acid halides can in turn be converted to esters, amides, anilides and other common derivatives by standard procedures.

The following examples are to be construed as illustrations of the preparation of the compounds of this invention and not as limitations thereof.

EXAMPLE I

Preparation of 1-(2'-chlorobenzyl)-3-carboxy-4,6-dimethylpyrid-2-one a. N-(2'-chlorobenzyl)-2-cyanoacetamide

A solution of 80.5 g. (0.71 mole) of ethyl cyanoacetate and 100 g. (0.71 mole) of 2-chlorobenzylamine in 200 ml. of absolute ethanol heated at reflux for 2 hours and then allowed to stand at ambient temperature overnight. The solvent is removed in vacuo and the residue is recrystallized from ether/pentane to give 56 g. (38% yield) of the desired product as a near white solid, m.p. 102°–4° C.; $\nu$3300 (NH), 2270 (CN), and 1650 cm.$^{-1}$ (C=O); $\delta$8.7 (broad, 1H, NH), 7.35 (broad s, 4H, aromatic protons), 4.40 (d, 2H, benzyl methylene) and 3.7 (broad s, 2H, CH$_2$CO).

Anal. Calc'd for C$_{10}$H$_9$Cl N$_2$O: C,57.57;H,4.35;N,13.43;Cl,16.99; O,7.66. Found: C,57.91;H,4.35;N,13.11;Cl,16.72; O,7.88 b. 1-(2'-chlorobenzyl)-3-cyano-4,6-dimethylpyrid-2-one

A solution of N-(2'-chlorobenzyl)-2-cyanoacetamide 179 g. (0.86 mole) and 2,4-pentanedione 86 g. (0.86 mole) in 500 ml. of 95% ethanol containing 10 ml. of piperidine is refluxed for 24 hours, after cooling the white crystalline product is isolated by vacuum filtration washed with ether and dried in vacuo to give 237.3 g. (87% yield) mp>250° C.;$\nu$2210 (CN) and 1650 cm.$^{-1}$(C=O).

c. 1-(2'-chlorobenzyl)-3-carboxy-4,6-dimethylpyrid-2-one 1-(2'-chlorobenzyl)-3-cyano-4,6-dimethylpyrid-2-one 151 g. (0.554 mole) is added to a mixture of 190 ml. of water and 380 ml. of conc. sulfuric acid and the mixture is heated overnight on a steam bath. The resulting solution is poured onto 6 liters of ice water and the solid precipitate is collected by filtration, washed with water and dried to give 218.8 g. (75% yield) mp 243–5° C.;$\nu$1730 cm$^{-1}$(C=O).

EXAMPLE II

Preparation of 1-(3'-chlorobenzyl)-3-carboxyl-4,6-dimethylpyrid-2-one a. N-(3'-chlorobenzyl)-2-cyanoacetamide

A solution of 38.5 g. (0.34 mole) of ethyl cyanoacetate and 48.1 g. (0.34 mole) of 3-chlorobenzylamine in 120 ml. of 95% ethanol is refluxed for 5 hours and then allowed to stand overnight at ambient temperature. Agitation causes crystallization. Filtration is followed by washing of the solid with a small amount of ether to give 28.7 g. of the desired product as small, white needles, m.p. 123°–5° C.

The filtrate is evaporated in vacuo and a solid is obtained by trituration of the oily residue with ether. The solid is isolated by filtration, slurried in 900 ml. of deionized water, reisolated by vacuum filtration and dried to give an additional 11.9 g. of product, m.p. 122°–4° C. yield: 40.6 g., 57%$\nu$3300 (NH), 2270 (CN) and 1660 cm.$^{-1}$(C=O);$\delta$8.87 (broad t, 1H, NH), 7.4 (broad s, 4H, phenyl protons), 4.37 (d, 2H, benzyl methylene); and 3.7 (s, 2H, CH$_2$CO).

Anal. Calc'd for C$_{10}$H$_9$ClN$_2$O: C,57.57;H,4.35;N,13.43;Cl,16.99. Found: C,57.94;H,4.36;N,13.42;Cl,77.21 b. 1-(3'-chlorobenzyl)-3-cyano-4,6-dimethylpyrid-2-one

Following the procedure of (Ib) above the product is isolated in 88% yield as white flakes, m.p. 163.5°–5° C.;$\nu$2220 (CN) and 1670 cm. (C=O);$\delta$7.0–7.6 (m, 4H, phenyl protons), 6.4 (s, 1H, olefinic proton), 5.35 (s, 2H, benzyl methylene), and 2.37 (s, 6H, methyls).

Anal. Calc'd for C$_{15}$H$_{13}$ClN$_2$O: C,66.06; H,4.80;N,10.27;Cl,13.00. Found: C,66.47;H,4.83;N,10.26;Cl,13.10.

c. 1-(3'-chlorobenzyl)-3-carboxy-4,6-dimethylpyrid-2-one

Following the procedure of (Ic) above the acid is similarly prepared in 34.4% yield as a white solid, m.p. 135°–7° C.;$\nu$1710 cm.$^{-1}$(C=O);$\delta$6.9–7.5 (m, 4H, phenyl protons), 6.55 (s, 1H, olefinic proton), 5.42 (s, 2H, benzyl methylene), and s, 3H, each methyls).

Anal. Calc'd for C$_{15}$H$_{14}$ClNO$_3$: C,61.76;H,4.84;N,4.80;Cl,12.15. Found: C,61.15;H,5.11;N,4.85;Cl,12.15.

EXAMPLE III

Preparation of 1-(2',4'-dichlorobenzyl)-3-carboxy-4,6-dimethylpyrid-2-one a. N-(2',4'-dichlorobenzyl)-2-cyanoacetamide

The product is obtained in 28% yield as a white solid, m.p. 119°–20° C., employing the same procedure as described for the preparation of (Ia) spectral parameters for this compound are as follows: $\nu$3340 (NH), 2280 (CN), and 1650 cm.$^{-1}$(C=O);$\delta$8.77 (broad t, 1H, NH), 7.60 and 7.40 (m and m, 1H, and 2H, phenyl protons), 4.38 (d, 2H, benzyl methylene), and 3.73 (s, 2H, CH$_2$CO).

Anal. Calc'd for C$_{10}$H$_8$Cl$_2$N$_2$O: C,49.44; H,3.32;N,11.52;Cl,29.17. Found: C,49.83;H,3.33;N,11.45;Cl,28.99.

b. 1-(2',4'-dichlorobenzyl)-3-cyano-4,6-dimethylpyrid-2-one

When the procedure of (Ib) is followed, a 95% yield of this product is obtained as a white solid, m.p.>250° C;$\nu$2230 (CN) and 1660 cm.$^{-1}$(C=O).

Anal. Calc'd for C$_{15}$H$_{12}$Cl$_2$N$_2$O: C,58.65;H,3.94;N,9.12;Cl,23.08. Found: C,58.54;H,4.12;N,9.13;Cl,23.04.

c. 1-(2',4'-dichlorobenzyl)-3-carboxy-4,6-dimethylpyrid-2-one

Following the procedure of (Ic), a 72.9% yield of this acid is analogously isolated as a white solid, m.p. 215°–7° C.;$\nu$1720 cm.$^{-1}$ (C=O).

EXAMPLE IV

Preparation of 1-(3',4'-dichlorobenzyl)-3-carboxy-4,6-dimethylpyrid-2-one a. N-(3',4'-dichlorobenzyl)-2-cyanoacetamide

A solution of 113.3 g. (1.002 moles) of ethyl cyanoacetate and 176.4 g. (1.002 moles) of 3,4-dichlorobenzylamine in 400 ml. of absolute ethanol is heated at reflux with stirring for 42 hours which upon cooling the entire solution solidifies. The latter is broken-up, slurried in ether, isolated by filtration and dried in vacuo to give 179.8 g. of product as a white solid, m.p. 144°–5° C.

A second crop (19.8 g) is obtained by concentration of the filtrate, slurrying the residue in ether and isolating as above.

Additional crops are similarly isolated to afford a total of 219.6 g. (91%) of product; $\nu$3330 (NH), 2270 (CN) and 1660 cm.$^{-1}$ (C=O); $\delta$8.85 (broad t, 1H, NH), 7.1–7.7 (m, 3H, phenyl protons), 4.35 (d, 2H, benzylmethylene), and 3.74 (s, 2H, CH$_2$CO).

Anal. Calc'd for $C_{10}H_8Cl_2N_2O$: C,49.44;H,3.32;N,11.52;Cl,29.17. Found: C,49.30;H,3.17;N,11.38;Cl,28.99.

b. 1-(3',4'-dichlorobenzyl)-3-cyano-4,6-dimethylpyrid-2-one

When the procedure in (Ib) is followed the product is isolated as white crystals in 96.5% yield: m.p. 177.5°–8.5° C.; $\nu$2220 (CN) and 1650 cm.$^{-1}$ (C=O); $\delta$7.0–7.7 (m, 3H, phenyl protons), 6.39 (s, 1H, olefinic proton), 5.32 (s, 2H, benzyl methylene), 2.35 (s, 6H, methyls).

Anal. Calc'd for $C_{15}H_{13}Cl_2NO_3$: C,55.23;H,4.02;N,4.29;Cl,21.74. Found: C,54.92;H,4.23;N,4.15;Cl,21.96.

c. 1-(3',4'-dichlorobenzyl)-3-carboxy-4,6-dimethylpyrid-2-one 1-(3',4'-dichlorobenzyl)-3-cyano-4,6-dimethylpyrid-2-one 170 g. (0.554 mole) is added to a mixture of 190 ml. of water and 380 ml of conc. sulfuric acid and heated overnight on a steam bath. The resulting tan solution is poured after cooling into 6 l of ice water and the precipitated solid is isolated by vacuum filtration. The crude product is slurried for a few hours in a solution of 4 moles of sodium hydroxide in 7 l of water and filtered. The filtrate is acidified with conc. hydrochloric acid and the solid product is collected by filtration, washed with water and dried to give 133 g. (73.4%) of the desired acid as a white solid, m.p. 139°–141° C.; $\nu$1720 cm.$^{-1}$ (C=O); $\delta$7.0–7.7 (m, 3H, phenyl protons), 6.53 (s, 1H, olefinic proton), 5.40 (s, 2H, benzyl methylene), and 2.53 and 2.36 (s and s, 3H each, methyls).

Anal. Calc'd for $C_{15}H_{13}Cl_2NO_3$: C,55.23;H,4.02;N,4.29;Cl,21.74. Found: C,54.92;H,4.23;N,4.15;Cl,21.96.

EXAMPLE V

Preparation of 1-(benzyl)-3-carboxy-4,6-dimethylpyrid-2-one a. N-benzyl-2-cyanoacetamide

A procedure analogous to that employed in the preparation of (IVa) is used to prepare this material. After 3 hours reflux the product is obtained as white needles: m.p. 123°–4.5° C., in 88.5% yield, $\nu$3340(NH), 2270 (CN), and 1650 cm.$^{-1}$ (C=O); $\delta$8.80 (broad, 1H, NH), 7.3 (s, 5H, phenyl protons), 4.35 (d, 2H, benzyl methylene), and 3.68 (s, 2H, CH$_2$CO).

b. 1-(benzyl)-3-cyano-4,6-dimethylpyrid-2-one

Following the procedure of (Ib) the product is obtained in 92.7% yield, m.p. 122°–3° C; $\nu$2220 (CN) and 1660 cm.$^{-1}$ (C=O); $\delta$7.1–7.6 (m, 5H, phenyl protons), 6.38 (s, 1H, olefinic proton), 5.40 (s, 2H, benzyl methylene), and 2.38 (s, 6H, methyls).

Anal. Calc'd. for $C_{15}H_{14}N_2O$: C,75.61;H,5.92;N,11.76. Found: C,75.77;H,5.88;N,11.93.

c. 1-(benzyl)-3-carboxy-4,6-dimethylpyrid-2-one 1-(benzyl)-3-cyano-4,6-dimethylpyrid-2-one 35.7 g., (0.15 mole) is added in one portion to a solution of 50 ml. of water and 100 ml. of conc. sulfuric acid. The mixture is heated on a steam bath for 24½ hr., cooled to room temperature and poured onto a mixture of 500 g. of ice in 500 ml. of water. After the ice has melted the white solid is extracted into methylene chloride, 600 ml., and the organic solution is filtered by gravity. Solvent removal followed by trituration of the residue with approximately 200 ml. of ether afforded 28.8 g. (74.6%) of the desired acid as a white solid m.p. 148°–53° C.; $\nu$1710 cm.$^{-1}$ (C=O); $\delta$7.0–7.6 (m, 5H, phenyl protons), 6.60 (s, 1H, olefinic proton), 5.47 (s, 2H, benzyl methylene), and 2.6 and 2.4 (s and s, 3H each, methyls).

EXAMPLE VI

Preparation of 1-(3-methylbenzyl)-3-carboxy-4,6-dimethylpyrid-2-one a. N-(3'-Methylbenzyl)-2-cyanoacetamide

A 75% yield of the desired product is obtained in a manner analogous to that utilized in the preparation of (Va). The amide is a white solid: m.p. 110°–12° C.; $\nu$3300 (NH), 2240 (CN), and 1630 cm.$^{-1}$ (C=O); $\delta$8.67 (broad, 1H, NH); 7.10 (broad s, 4H, phenyl protons), 4.26 (d, 2H, benzyl methylene), 3.63 (s, 2H, CH$_2$CO) and (s, 3H, CH$_3$).

Anal. Calc'd for $C_{11}H_{12}N_2O$: C,70.19;H,6.43;N,14.88. Found: C,70.11;H,6.38;N,15.01.

b. 1-(3'-methylbenzyl)-3-cyano-4,6-dimethylpyrid-2-one

When the procedure of (Ib) is followed a 93% yield of product is obtained as a white solid: m.p. 156°–8° C.; $\nu$2200 (CN) and 1650 cm.$^{-1}$ (C=O); $\delta$6.8–7.4 (m, 4H, phenyl protons), 6.34 (s, 1H, olefinic proton), 5.30 (s, 2H, benzyl methylene), and 2.33 and 2.27 (s, and s, 6H and 3H, resp., methyls).

Anal. Calc'd for $C_{16}H_{16}N_2O$: C,76.16;H,6.39;N,11.10. Found: C,76.13;H,6.22;N,11.15.

EXAMPLE VII

Preparation of 1-(4-methylbenzyl)-3-carboxy-4,6-dimethylpyrid-2-one a. N-(4-methylbenzyl)-2-cyanoacetamide

A solution of 93 g. (0.825 mole) of ethyl cyanoacetate and 100 g. (0.825 mole) of 4-methylbenzylamine in 150 ml. of 2-methoxyethanol is refluxed for 2 hr. After cooling the solid product is isolated by vacuum filtration, washed with pentane and dried to give 90 g. (57.6%) of amide as a white solid: m.p. 124°–6° C.;ν3220 (NH), 2230 (CN), and 1630 cm.$^{-1}$(C=O)δ8.77 broad, 1H, NH); 7.17 (s, 4H, phenyl protons), 4.28 (d, 2H, benzyl methylene), 3.67 (s, 2H, CH$_2$CO), and 2.28 (s, 3H, CH$_3$).

Anal. Calc'd for C$_{11}$H$_{12}$N$_2$O: C,70.19;H,6.43;N,14.88. Found: C,69.73;H,6.42;N,14.75.

b. 1-(4-methylbenzyl)-3-cyano-4,6-dimethylpyrid-2-one

When the procedure of (Ib) is followed this compound is isolated in 88.6% yield as a white solid, m.p. 151°–2° C; ν2210 (CN) and 1645 cm.$^{-1}$ (C=O);δ7.10 (broad s, 4H, phenyl protons), 6.33 (s, 1H, olefinic protons), 5.27 (s, 2H, benzyl methylene), and 2.33 and 2.28 (s and s, 6H and 3H, resp., methyls).

Anal. Calc'd for C$_{16}$H$_{16}$N$_2$O: C,76.16;H,6.39;N,11.10. Found: C,75.95;H,6.21;N,11.01.

c. 1-(4-methylbenzyl)-3-carboxy-4,6-dimethylpyrid-2-one 1-(4-methylbenzyl)-3-cyano-4,6-dimethylpyrid-2-one 90 g. (0.357 mole) in a mixture of 146 ml. of water and 243 ml. of conc. sulfuric acid is heated on a steam bath for 22 hr. After cooling the dark solution is poured into 3 l of ice water and the resulting solid is extracted into methylene chloride. The organic solution is filtered and stripped to dryness in vacuo. The solid residue is pulverized under ether. Filtration gives 60 g. (6%) of acid as a near white solid: m.p. 178°–81° C. Final purification by the usual base extraction/acidification gave a 93% recovery of pure product: m.p. 184°–6° C. ν1710 cm.$^{-1}$ (C=O);δ7.15 (broad s, 4H, phenyl protons), 5.41 (s, 2H, benzyl methylene), 2.6, 2.6, 2.4 and 2.28 (all s, 3H each, methyls).

Anal. Calc'd for C$_{16}$H$_{17}$NO$_3$: C,70.83;H,6.32;N,5.16. Found: C,70.65;H,6.34;N,5.17.

EXAMPLE VIII

Preparation of 1-(2,4-dimethylbenzyl)-3-carboxy-4,6-dimethylpyrid-2-one a. N-(2,4-dimethylbenzyl)-2-cyanoacetamide This amide is prepared in 69% yield in a fashion analogous to the synthesis of (VIa). The white solid product melts at 137°–9° C. ν3250 (NH) and 1670 cm.$^{-1}$ (C=O). The CN stretching band is too weak to observe. NMR data are: δ8.5 (broad, 1H, NH), 7.02 (m, 3H, phenyl),4.22 (d,2H, benzyl methylene), 3.6 (s, 2H, CH$_2$CO) and 2.22 (s, 6H, methyls).

Anal. Calc'd for C$_{12}$H$_{14}$N$_2$O: C,71.26;H,6.98;N,13.85. Found: C,71.35;H,6.93 N,14.00.

b. 1-(2,4-dimethylbenzyl)-3-cyano-4,6-dimethylpyrid-2-one

From 44 g. of the corresponding cyanoacetamide is obtained 54g. of product. Recrystallization from methanol affords an 80% recovery of pure product as white needles: m.p. 211° –3° C; ν2220 (CN) and 1650 cm.$^{-1}$ (C=O); δ6.9-7.2 (unresolved, 2H, aromatic protons), 6.2-6.5 (s and partially buried d, 2H total, olefinic proton and one aromatic proton), 5.23 (s, 2H, benzyl methylene), 2.0–2.5 (m, 12H, methyls).

Anal. Calc'd for C$_{17}$H$_{18}$N$_2$O: C,76.66;H,6.81;N,10.52. Found: C,76.77;H,6.79;N,11.01.

c. 1-(2,4-dimethylbenzyl)-3-carboxy-4,6-dimethylpyrid-2-one

This acid is prepared in 18.4% yield, m.p. 186°–8° C., in a manner similar to the preparation of (VIIc): ν1720 cm.$^{-1}$(C=O); δ6.7–7.2 (m, 2H, phenyl protons), 6.67 (s, 1H, olefinic proton), 6.36 (d, 1H, phenyl proton), 5.35 (s, 2H, benzyl methylene), 2.62 (s, 3H, methyl), 2.37 (s, 6H, methyls), and 2.27 (s, 3H, methyl).

Anal. Calc'd for C$_{17}$H$_{19}$NO$_3$: C,71.56;H,6.71;N,4.91. Found: C70.59;H,6.72;N,4.85.

EXAMPLE IX

Preparation of 1-(3'4-dimethylbenzyl)-3-carboxy-4,6-dimethyl-pyrid-2-one a. N-(3,4-dimethylbenzyl)-2-cyanoacetamide This amide is isolated in 53% yield in a procedure similar to the preparation of (IVa): m.p. 137°–9° C; ν3300 (NH) and 1645 cm.−1 (C=O), the CN stretch is indistinct; δ8.66 (broad, 1H, NH), 7.0 (broad s, 3H, phenyl), 4.22 (d, 2H, benzyl methylene), 3.63 (s, 2H, CH$_2$CO), and 2.2 (s, 6H, methyls).

Anal. Calc'd for C$_{12}$H$_{14}$N$_2$O: C,71.26;H,6.98;N,13.85. Found: C71.44;H,7.05;N,13.96.

b. 1-(3,4-dimethylbenzyl)-3-cyano-4,6-dimethylpyrid-2-one

Following the procedure of (Ib) 81% yield of product is isolated as a white solid, m.p. 174°–6° C.; ν2210 (CN) and 1660 cm.$^{-1}$ (C=O); δ6.8–7.3 (m, 3H, phenyl protons), 6.33 (s, 1H, olefinic proton), 5.26 (s, 2H, benzyl methylene), and 2.36 and 2.20 (s and s, 6H each, methyls).

Anal. Calc'd for C$_{17}$H$_{18}$N$_2$O: C,76.66;H,6.81;N,10.52. Found: C,76.7H,7.12;N,10.43.

c. 1-(3,4-dimethylbenzyl)-3-carboxy-4,6-dimethylpyrid-2-one

When the procedure of (VIIc) is followed a 32.6% yield of product is obtained mp 194°–6° C; ν1705 cm.$^{-1}$ (C=O); δ6.8–7.4 (m, 3H, phenyl protons), 6.33 (s, 1H, olefinic proton), 5.38 (s, 2H, benzylmethylene), 2.73 (s, 3H, methyl, 2.42 (s, 3H, methyl), and 2.23 (s, 6H, two methyls).

EXAMPLE X

Preparation of 1-(3-,4-dichlorobenzyl)-3-carboxypyrid-2-one a. Diethyl 3-ethoxyallylidenemalonate To a stirred, refluxing solution of 1.0 g. of freshly fused zinc chloride in 220 g. (1.0 mole) of 1,1,3,3-tetraethoxypropane and 200 g. (1.96 moles) of acetic anhydride is added dropwise during 3 hr. 10 min. 91 g. (0.57 mole) of diethyl malonate. After addition is complete, the reaction mixture is refluxed for ½ hour after which time the lower boiling components of the reaction mixture are removed by distillation up to a vapor temperature of 120° C. (pot 130° C.). An additional 50 ml. of acetic anhydride are added and reflux is continued for 16 hr. Again, low boilers are removed and desired product is isolated from the residue by vacuum distillation. There is obtained 120 g. (87%) of product as a yellow oil: b.p. 110°–128°/0.1–1.7 mm. ν(film) 1720 (C=O) and 1610 cm.$^{-1}$ (C=O); δ$_{CDCl_3}$$^{TMS}$ 7.47, 7.13, 6.25 (s, s, t, 1H each, olefinic protons), 3.84–4.6 (m, 6H, ethyl methylene) and 1.35 (overlapping triplets, 9H, ethyl methyls).

b. 1-(3,4-dichlorobenzyl)-3-carboxypridin-2-one ethyl ester

To a stirred, cooled (0° C) solution of 30 g. (0.124 mole) of diethyl ethoxyallylidenemalonate in 75 ml. of absolute ethanol is added dropwise during 30 min. a solution of 23.8g. (0.136 mole) of 3,4-dichlorobenzlamine in 25 ml. of the same solvent. After addition is complete the solution is allowed to warm to ambient temperature resulting in the precipitation of product. The mixture is diluted with an additional 100 ml. of ethanol and is allowed to stir at ambient temperature overnight.

Addition of 2 ml. of piperidine followed by 2 hr. reflux gives a red solution which upon cooling deposits the product as a yellowish solid. The slurry is diluted with 300 ml. of hexane and the whole is stirred for 30 min. The solid is isolated by filtration and dried in air at 40°–50° to give 29 g. (63%) of product as a near white solid: m.p. 140°–142° C.; ν1720 cm.$^{-1}$ (C=O); δ(TMS, CDCl$_3$)8.20 (dd, 1H, H$_6$), 7.76 (dd, 1H, H$_4$), 7.1–7.6 (m, 3H, aromatic protons), 6.33 (t, 1H, H$_5$), 5.16 (s, 2H, benzyl methylene), 4.36 and 1.35 (q and t, ethyl group).

Anal. Calc'd for C$_{15}$H$_{13}$Cl$_2$NO$_3$: C,55.24;H,4.01;N,4.29;Cl,21.73. Found: C,55.33;H,4.18;N,4.22;Cl,21.79.

EXAMPLE XI

Preparation of 1-(3,4-dichlorobenzyl-3-carboxy-5-methyl pyrid-2-one a. 1.1.3.3-tetraethoxy-2-methylpropane A solution of one equivalent of diethoxymethyl acetate and one equivalent of a ethyl propenyl ether/ethanol mixture is stirred at ambient temperature for 30 min. followed by the addition of 1.3 equivalents of triethyl orthoformate. After cooling to 5° C. 1.5 ml. of boron trifluoride etherate is added and the resulting exotherm (5° to 37° C.) is controlled with an ice bath. After stirring at ambient temperature overnight the yellow reaction solution is diluted with ether and washed with water, saturated aqueous sodium bicarbonate and again with water. Drying (MgSO$_4$) followed by solvent removal afforded a 92% yield of oil which is shown by glc to be ~80% pure product, δ(TMS, CDCl$_3$) 4.44 (d, 2H, CH—O); 3.3–4.0 (complex, 8H, ethyl methylene, ~2.1 (m, 1H, CH$_{3-CH}$), 1.1 (t, 12H, ethyl methyls), and 1.0 (d, 3H, CH$_3$—CH).

b. diethyl 3-ethoxy-2-methylallylidenemalonate

Prepared in 65.4% yield from (XIa) in a manner analogous to that employed in the preparation (Xa) described above, νfilm 1720 (C=O) and 1600 cm.$^{-1}$ (C=C); δ(TMS, CDCl$_3$) 7.10 (s, H, olefinic proton), 6.77 (broad, 1H, olefinic proton), 3.8–4.6 (complex, 6H, ethyl methylenes), 1.72 (J=2Hz, 3H, methyl), and 1.33 (complex t, 9H, ethyl methyls).

c. 1-(3,4-dichlorobenzyl)-3-carboxy-5-methylpyrid-2-one ethyl ester

To a stirred solution of 30g. (0.117 mole) of (XIb) in 75 ml. of absolute ethanol is added 22.7g. (0.129 mole) of 3,4-dichlorobenzylamine in 25 ml. of the same solvent at ambient temperature over the course of 4 min. After stirring for 3 hr. 45 min., 2ml. of piperidine are added and the orange solution is heated to reflux. After boiling for 24 hr. another 1 ml. of piperidine is added and reflux is continued for 1 more hour. Solvent removal in vacuo gives a viscous oil which is not further purified.

d. 1-(3,4-dichlorobenzyl)-3-carboxy-5-methylpyrid-2-one

Hydrolsis of (XIc) gives the product in 30% yield as a slightly off white solid: m.p. 216°–218° C.; 1725 cm.$^{-1}$ (C=O); δ8.3 (broad s, 2H, H$_4$ and H$_6$), 7.3–7.8 (m, 3H, phenyl protons), 5.3 (s, 2H, benzyl methylene), and 2.2 (s, 3H, methyl).

Anal. Calc'd for C$_{14}$H$_{11}$Cl$_2$NO$_3$: C,53.86; H, 3.56; N, 4.48; Cl, 22.72. Found: C, 53.50; H, 3.51; N, 4.29; Cl, 22.91 C, 53.84; H, 3.32; N, 4.53.

EXAMPLE XII

Preparation of 1-(3,4-dichlorobenzyl)-3-carboxy-4-methylpyrid-2-one a. N-(3,4-dichlorobenzyl)-2-cyano-3-methylcrotonamide A mixture of 60.8 g (0.25 mole) of IVa, 70.0 g. (1.2 moles) of acetone, 20 g of ammonium acetate and 45 g. of acetic acid is heated to reflux in 250 ml. of benzene under a Barrett water separator. All solids dissolved and the resulting clear solution became turbid as water evolution began. Reflux is hated after 12 ml of aqueous phase has been collected. Solvent removal is followed by dissolution in methylene chloride, neutralization with aqueous sodium bicarbonate, drying and evaporation of the methylene chloride gives 65.0 g (92%) of product as a tan solid. Recrystallization from ethyl acetate/ether gives white fibers: m.p. 131 °–132.5° C.; ν3350 (NH), 2220 (CN) and 1670 cm.$^{-1}$(C=O); δ9.04 (broad t, 1H, NH), 7.2–7.8 (m, 3H, phenyl protons), 4.43 (d, 2H, benzyl methylene), and 2.17 and 2.11 (two s, 6H total, methyls).

Anal. Calc'd for C$_{13}$H$_{12}$Cl$_2$N$_2$O: C,55.14;H,4.27;N,9.89;Cl,25.04. Found: C,55.02;H,4.36;N,9.90;Cl,24.91.

b. 1-(3,4-dichlorobenzyl)-3-cyano-4-methylpyrid-2-one

A solution of 42.8 g. (0.15 mole) of N-(3,4-dichlorobenzyl)-2-cyano-3-methylcrotonamide and 18.0 g (0.15 mole) of N,N-dimethylformamide dimethyl acetal in 250 ml. of tetrahydrofuran is stirred at ambient temperature for 22 hr. followed by 1 hr. at reflux. The solvent is removed and the tacky solid residue is heated until molten. When evolution of dimethylamine subsides the reaction mixture is allowed to cool and the dark glassy residue is recrystallized from ethanol. The solid product is slurried in ether and isolated by filtration to give 15.79 g. (36%) of product as a brown powder: m.p. 177.5°–180.5° C; ν (ethanol) 2210 (CN) and 1670 cm.$^{-1}$ (C=O); δ8.19(d, 1H, H$_6$), 7.2–7.8 (m, 3H, aromatic protons), 6.46 (d, 1H, H$_5$), 5.16 (s, 2H, benzyl methylene), and 2.4 (s, 3H, methyl).

Anal. Calc'd for C$_{14}$H$_{10}$Cl$_2$N$_2$O: C,57.36;H,3.44;N,9.56;Cl,24.19. Found: C,57.49;H,3.60;N,9.56;Cl,23.85.

c.
1-(3,4-dichlorobenzyl)-3-carboxy-4-methylpyrid-2-one

A solution of 11.5 g. (0.039 mole) of 1-(3,4-dichlorobenzyl)-3-cyano-4-methylpyrid-2-one in a mixture of 50 ml. of water and 100 ml. of conc. sulfuric acid heated overnight on a steam bath. Addition of the reaction mixture ot 3.1 of ice water results in the precipitation of product which is collected by filtration, washed with water and air dried at 40°–50° C. for 18 hr. to give 11 g. (90%) of product as a tan solid:m.p. 219°–221° C.; $\nu$1710 cm.$^{-1}$(C=O); 8.19 (d, 1H, H$_6$), 7.2–7.8 (m, 3H, phenyl protons), 6.59 (d, 1H, H$_5$), 5.26 (s, 2H, benzyl methylene) and 2.51 (s, 3H, methyl).

Anal. Calc'd for $C_{14}H_{11}Cl_2NO_3$: C,53.86; H, 3.56; N,4.48; Cl, 22.72. Found: C,53.78; N,3.72; N,5.25; Cl,22.46.

EXAMPLE XIII

Preparation of
1-(3,4-dichlorobenzyl)-3-carboxy-6-methylpyrid-2-one a. N-(3,4-dichlorobenzyl)-2-cyanoacetamide

This compound was prepared according to the procedure of (IVa)

b. 1-(3,4-dichlorobenzyl)-3-cyano-6-methylpyrid-2-one

A solution of 49.7 g. (0.204 mole) of N-(3,4-dichlorobenzyl)-2-cyanoacetamide, 48.0 g (0.48 mole) of 4-methoxy-3-buten-2-one, and 4 g. of 1,4-diazabicyclo (2.2.2)octane (DABCO) in 160 ml. of 2-methoxyethanol is refluxed for 4 hr. The dark reaction mixture is then concentrated in vacuo and the crude solid is isolated by filtration from the resulting slurry and washed with ether. The crude product is dissolved in methylene chloride and the organic solution is washed with water, 2N—HCl and finally with more water. The methylene chloride is removed and the product is obtained in 62% yield by ether tirituration.

Final purification can be achieved by dissolution of the product in methylene chloride, slurrying it with silica gel, filering, removing the solvent and recrystallizing the residue from ethanol. The product is obtained as yellow needles; m.p. 161°–162.5° C.;$\nu$2230 (CN) and 1650 cm.$^{-1}$ (C=O);$\delta$8.10 (d,1H, H$_4$), 7.0–7.7 (m, 3H, phenyl protons), 6.4 (d, 1H, H$_5$), 5.37 (s, 2H, benzyl methylene), and 2.43 (s, 3H, methyl).

c. 1-(3,4-dichlorobenzyl)-3-carboxy-6-methylpyrid-2-one

Following the procedure of (XIIc) the product is obtained in 90% yield as a tan powder: m.p. 154°–156° C.; $\nu$1710 cm.$^{-1}$ (C=O); $\delta$8.5(d, 1H, H$_4$), 7.1–7.8 (m, 3H, aromatic protons), 6.84 (d, 1H, H$_5$), 5.59 (s, 2H, benzyl methylene) and 2.57 (s, 3H, methyl).

Anal. Calc'd for $C_{14}H_{11}Cl_2NO_3$: C,53.86;H,3.56;N,4.48;Cl,22.72. Found: C,54.06;H,3.55;N,4.41;Cl,22.80.

EXAMPLE XIV 1-(benzyl)-3-carboxy-5-methylpyrid-2-one

Following the procedure of XIA, XIb, XIc and XId this acid is obtained as a brown solid: m.p. 173°–5° C.;$\nu$1730 cm$^{-1}$ (C=O); $\delta$8.33 (broad, 2H, H$_4$and H$_6$), 7.40 (s, 5H, phenyl protons), 5.33 (s, 2H, benzyl methylene), and 2.1 (s, 3H, methyl).

Anal. Calc'd for $C_{14}H_{13}NO_3$: C, 69.12; H, 5.39; N, 5.76. Found: C,69.31;H,5.70;N,5.46.

EXAMPLE XV a. Sodium Hydride Method

To a stirred slurry of approx. 0.30 mole of the appropriate carboxlic acid in 300 ml. of dry 1,2-dimethylethane is added one equivalent of sodium hydride (oil dispersion). After stirring for several hours the mixture is diluted with 1 ml. of methanol and 300 ml. of ether. The solid product is isolated by filtration and dried in vacuo.

The following salts are made according to this procedure.

Sodium salt of
1-(2-chlorobenzyl)-3-carboxy-4,6-dimethylpyrid-2-one

Quantitative yield of tan powder, m.p. 208°–10° C. dec.;$\nu$1650 cm.$^{-1}$(C=O);$\delta$D$_2$O (shifts given in Hz from HOD peak) —148 to —170 (m, 3H, phenyl protons), —114 to —132 (m, 1H, phenyl proton), —98 (s, 1H, olefinic proton), —43 (s, 2H, benzyl methylene), and +147 (s, 6H, methyls).

Sodium salt of
1-(chlorobenzyl)-3-carboxy-4,6-dimethylpyrid-2-one

Quantitative yield of tan powder, m.p. 248°–50° C. dec.;$\nu$1650 cm.$^{-1}$ (C=O).

Sodium salt of
1-(2,4-dichlorobenzyl)-3-carboxy-4-6-dimethylpyrid-2-one

Quantitative yield of white powder, m.p. 185°–7° C.;$\nu$1660 cm.$^{-1}$ (C=O).

Sodium salt of
(3,4-dichlorobenzyl)-3-carboxy-4,6-dimethylpyrid-2-one

This product is obtained as a tan solid in quantative yield m.p. 172°–4° C.;$\nu$1660 cm.$^{-1}$(C=O).

Sodium salt of
(3,4-dichlorobenzyl)-3-carboxy-6-methyl-pyrid-2-one

A 93.5% yield of a white powder m.p. 201°–3° C. is obtained; $\nu$1660 cm$^{-1}$ (C=O); $\delta$D$_2$O 7.76 (d, 1H, H$_4$); 6.9–7.4 (m, 3H, aromatic protons), 6.16 (d, 1H, H$_5$), 5.2 (broad s, 2H, benzyl methylene), 2.13 (s, 3H, methyl).

Sodium Hydroxide/Methanol Method

The sodium salt, is preparedby dissolving the carboxylic acid in methanol containing one equivalent of sodium hydroxide. Solvent removal followed by ether trituration and filtration affords the product as a white powder, m.p. 170° C.;$\nu$1660 cm$^{-1}$(C=O);$\delta$D$_2$O 6.9–7.5 (m, 3H, phenyl protons) 6.23 (s, 1H, olefinic proton), 5.32 (s, 2H, benzyl methylene), and 2.23 and 2.19 (two s, 6H total, methyls).

Sodium salt of
1-(benzyl)-3-carboxy-4,6-dimethyl-pyrid-2-one

Quantitative yield of white powder m.p. 241°–3° C.; $\nu$1645 cm.$^{-1}$(C=O).

Sodium salt of
1-(4-methylbenzyl)-3-carboxy-4,6-dimethylpyrid-2-one.

A 75% yield of brown solid, m.p. 230°–1° C., was obtained; 1650 cm.$^{-1}$(C=O).

Sodium salt of 1-(2,4-dimethylbenzyl)-3-carboxy-4,6-dimethylpyrid-2-one.

A 99% yield of brown solid, m.p. 208°–10° C; $\nu$1655 cm.$^{-1}$(C=O).

Sodium salt of 1-(3,4-dimethylbenzyl-3-carboxy-4,6-dimethylpyrid-2-one.

An 81% yield of tan solid, m.p. 226°–8° C.; $\nu$1645 cm.$^{-1}$(C=O).

Sodium salt of 1-(3,4-dichlorobenzyl)-3-carboxy-4 methylpyrid-2-one.

Obtained an 82% yield of a brown solid m.p. 228°–230° C.; $\nu$1655 cm.$^{-1}$(C=O); D$_2$O 7.1–7.6 (unresolved, 4H, aromatic protons and H$_6$), 6.3 (d, 1H, H$_5$), 5.07 (broad s, 2H, benzyl methylene, and 2.1 (s, 3H, methyl).

c. Sodium Methoxide/Methanol Method

Sodium salt of 1-(benzyl)-3-carboxy-5-methylpyrid-2-one

Treatment of the acid with sodium methoxide in methanol gave a brownish solid in 88% yield: m.p. 172°–74° C.; $\nu$1680 cm.$^{-1}$(C=O); $\delta$D$_2$O 7.68 (broad s, 1H, H$_6$), 7.33 (broad s, 6H, phenyl protons and H$_4$), 5.11 (s, 2H, benzyl methylene), 2.03 (s, 3H, methyl).

When the procedures in the above examples are followed and the appropriate starting materials are used, the following compounds can be prepared.

1-benzyl-3-carboxy-6-methylpyrid-2-one
1-(2-chlorobenzyl)-3-carboxy-4,6-dimethylpyrid-2-one
1-(3-bromobenzyl)-3-carboxy-6-methylpyrid-2-one
1-(4-nitrobenzyl)-3-carboxy-4,6-dimethylpyrid-2-one
1-(2,4-dichlorobenzyl)-3-carboxy-4,6-dimethylpyrid-2-one
1-(3,4-dichlorobenzyl)-3-carboxy-4,6-dimethylpyrid-2-one
1-(2,5-dibromobenzyl)-3-carboxy-6-ethylpyrid-2-one
1-(4-trifluoromethylbenzyl)-3-carboxy-4,6-diethylpyrid-2-one and physiologically acceptable salts thereof
1-(2-methylbenzyl)-3-cyano-4,6dimethylpyrid-2-one
1-(3-ethylbenzyl)-3-cyano-6-methylpyrid-2-one
1-(4-isopropylbenzyl)-3-carbamoyl-6-ethylpyrid-2-one
1-(2,4-dimethylbenzyl)-3-carbamoyl-4,6-dimethylpyrid-2-one
1-(2,5-diethylbenzyl)-3-carbomethoxy-4,6-dimethylpyrid-2-one
1-(3,4-dimethylbenzyl)-3-carboethoxy-4,6-dimethylpyrid-2-one
1-(2-aminobenzyl)-3-carbomethoxy-6-methylpyrid-2-one The compounds of this invention have been found to produce a variety of plant growth regulatory responses. These responses are observed when the compounds alone or in a carrier or as formulations are applied to the plant itself, as by foliar application, or to plant parts such as by seed treatment or to the environment or habitat of the plant, such as by soil drenching or soil incorporation. The most outstanding plant growth influencing property is suppression of growth, i.e., stem elongation is inhibited. In other instances flowering or seed formation is altered. In other cases malformation of leaves is noted. Sometimes particularly at high dosages, a plant species may be herbicidally sensitive.

Preemergence herbicidal activity has also been obtained. Individual plant species give different types of responses and any one or several of these plant responses may be observed for any given species. The major contribution of the compounds of this invention to the field of plant growth regulation is that they provide non-injurious plant growth regulants which inhibit stem elongation of many weed, crop and woody species and alter flowering and fruit development.

To obtain hybrid seed, the following procedure is generally employed. The two parents to be crossed are planted in alternate strips. The female parent is treated with a compound of the invention. The male-sterile female parent thus produced will be pollinated by pollen from the other, male-fertile, male parent, and the seed produced by the female parent will be hybrid seed which can then be harvested by conventional means.

A test was run to study gametocidal activity. For this test, the compound is applied as an aqueous solution to the plane in five different stages of growth from young seedlings up to and including the boot stage of development. Plants are sprayed to run-off with various dosage rates. When the plants reached the flowering stage of development, each spike or seed head is covered with a paper bag to prevent cross pollination. In those instances where the treatments delayed flowering, the spikes are not covered with paper bags because viable pollen from the nonsprayed checks would no longer be available at these later dates. The most positive results are obtained with the plants in the boot stage.

No seed is produced in those spikes which are covered to prevent cross pollination. This absence of seeds indicates that fertilization has not taken place and that male sterility has been induced with the topical applications of the sodium salt of the compound. The presence of seed in a few treated seed heads that are covered further indicates that cross pollination has occurred and the treatment has not affected the female portion of the spikelet. The higher dosage rates delays the time of flowering; thus, no pollen is available at this time for cross pollination since the non-treated check plants have flowered at an earlier date.

A soil drench test is used as one method for evaluating the plant growth regulating properties of the compounds of this invention. In this test, seeds or plants are planted in pots and at a given stage of growth the soil is watered with a preparation containing the compound at given dosages in terms of pounds per acre. Growth responses are subsequently observed.

For foliage spray tests, the compounds are dissolved in an appropriate solvent, usually acetone for the amides, acids and esters, and water for the salts and sprayed onto the foliage at a given dosage per acre in a carrier volume of about 50 gallons per acre. Growth responses are subsequently observed.

In seed treatment tests an aqueous solution or suspension of the test compound is prepared and diluted to various percent concentrations. Seeds are then immerssed in these preparations for about 20 hours, after which they are washed with water, planted in untreated soil, and the germination and growth is subsequently observed.

When the compounds of this invention are applied to plants or to the habitat of plants, they give a growth regulating response in the dosage range of about 0.01 to 30 pounds per acre (0.011 to 33 kilos per hectare). At the higher dosages, herbicidal responses can be manifested. Depending on the type of response desired the amount will vary with the plant species to be treated. Generally, the preferred range is from 0.05 to 15 pounds per acre. Seeds can be treated with the compounds themselves or with any concentration of a solution of formulation of them.

The compounds of this invention can be employed as plants growth response agents either individually or as a mixture of two or more of them. They also can be used in combination with other plant growth regulatory compounds such as maleic hydrazide, succinic acid, 2,2-dimethylhydrazide, choline and its salts, 2-chloroethyltrimethylammonium chloride, triiodobenzoic acid, tributyl-2,4-dichlorobenzylphosphonium chloride, polymeric N-vinyl-2-oxazolidinones, tri(dimethylaminoethyl)phosphate and its salts, and N-dimethylamino-1,2,3,6-tetrahydrophthalamic acid and its salts. The compounds of this invention can also be combined with a herbicide for use on plants which are not sensitive to the herbicide at weed controlling rates. For example, they can be combined with 2,4-D for use on monocotyledonous plants such as cereals and turf grasses, with 3′4′-dichloropropionanilide for use on rice or with 2,4-dichlorophenyl 4-nitrophenylether for use on rice and other cereals.

The compounds of this invention can be applied in liquid carriers. One preferred group of the compounds are the water soluble salts, in which case water is the preferred carrier. Nonphytotoxic organic solvents such as ketones, alcohols, glycols, dimethyl-formamide and dimethyl sulfoxide can be employed. If desired a surfactant such as a wetting agent can also be used and this usually constitutes a minor part (in general less than 10%) of the solution or formulation. The surface active agents can be anionic, cationic, or non-ionic. For the water-soluble salts cationic and non-ionic surfactants are preferred. Commonly used surfactants are well known in the art and can be found in John W. McCutcheon's publication: "Detergents and Emulsifier, Annual," John W. McCutcheon Inc., Morristown, N. J.

The compounds of this invention can be formulated in various ways as for example emulsifiable concentrates, wettable powders, dusts, granules and pellets. Usually for application to the plant or plant parts or the plant habitat, the formulations are extended with a suitable carrier. Emulsifiable concentrates are most usually extended with a liquid carrier such as water and dusts; granules and pellets are most usually extracted with a solid carrier such as mineral clays.

Emulsifiable concentrates can be made by dissolving the compounds in an organic solvent and adding one or more solvent-soluble emulsifying agents. Suitable solvents are usually water-immiscible and can be found in the hydrocarbon chlorinated hydrocarbon, ketone, ester, alcohol and amide classes of organic solvents.

Wettable powders can be made by incorporating the compounds in an inert, finely divided solid carrier along with a surfactant which can be one or more emulsifying, wetting, dispersing or spreading agents or blends of these. Suitable carriers can be found in the classes of clays, silicates, silicas, limes, carbonates and organic carriers.

Solid compositions in the form of dusts can be made by compounding the compounds of this invention with inert carriers conventionally employed for the manufacture of pesticidal dusts for agricultural use, such as talcs, finely particled clays, pyrophyllite, diatomaceous earth, magnesium carbonate, wood or walnut shell flours.

Granular or pelletized formulations can be made by incorporating the compounds into granular or pelletized forms of agronomically acceptable carriers such as granular clays, vermiculite, charcoal, ground corncobs or bran.

The growth regulatory action of the compounds of the present invention can be advantageously employed in various ways. The production of shorter and thicker stems in cereal grains reduces the tendency toward lodging. Turf grasses can be maintained at a low height and the necessity for frequent mowing alleviated. The plant growth on embankments, such as roadsides, can be controlled to prevent erosion and at the same time maintain its aesthetic value. There can be an advantage in producing a dormant period in certain plants. The control of flowering and fruiting can be advantageous in the production of seedless fruit and for hybridization. Delaying the vegetative process or altering the time of flowering and fruiting can result in more advantageous harvest dates or increased flower, fruit and/or seed production. The chemical pruning of trees, shrubs, ornamentals and nursery stock can be beneficial. Other applications of the compounds of the present invention suggest themselves to those skilled in the art of agriculture and horticulture.

We claim:

1. A compound of the formula:

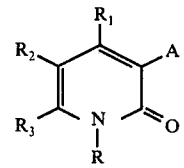

wherein A is cyano; $R_1$, $R_2$, $R_3$ are hydrogen, methyl or ethyl; R is a group of the formula:

wherein X is hydrogen, $NH_2$, halogen, trifluoromethyl, nitro, or $(C_1-C_4)$ alkyl; $n$ is 0–2.

* * * * *